United States Patent [19]

Hentschel et al.

[11] 4,259,487

[45] Mar. 31, 1981

[54] PROCESS FOR THE PRODUCTION OF OPTIONALLY SUBSTITUTED 2-MERCAPTO-4,6-DI-CHLORO-S-TRIAZINES

[75] Inventors: Klaus Hentschel, Kalmthout, Belgium; Friedrich Bittner, Bad Soden, Fed. Rep. of Germany

[73] Assignee: Deutsche Gold- und Silber-Scheideanstalt vormals Roessler, Frankfurt, Fed. Rep. of Germany

[21] Appl. No.: 94,802

[22] Filed: Nov. 15, 1979

[30] Foreign Application Priority Data

Nov. 20, 1978 [DE] Fed. Rep. of Germany ....... 2850332

[51] Int. Cl.³ .......................................... C07D 251/38
[52] U.S. Cl. ................................................. 544/218
[58] Field of Search ........................................ 544/218

[56] References Cited

U.S. PATENT DOCUMENTS

| 2,911,337 | 11/1959 | Uhlenbroek et al. ............ 544/218 X |
| 3,577,416 | 5/1971 | Schwärze et al. ............... 544/218 X |
| 3,925,377 | 12/1975 | Geiger et al. .................. 544/191 OR |

FOREIGN PATENT DOCUMENTS

| 1076696 | 3/1960 | Fed. Rep. of Germany ... 544/218 OR |
| 1964619 | 7/1970 | Fed. Rep. of Germany ........... 544/194 |
| 1670585 | 2/1972 | Fed. Rep. of Germany ........... 544/218 |
| 2332636 | 1/1975 | Fed. Rep. of Germany ... 544/191 OR |

*Primary Examiner*—John D. Randolph

[57] ABSTRACT

2-mercapto-4,6-dichloro-s-triazines or substituted 2-mercapto-4,6-dichloro-s-triazines are produced by the known reaction of cyanuric chloride with a mercaptan or mercaptide in the presence of an acid binding agent in an improved manner by working at high mixing velocities and thus at high reaction speed and thereby obtaining high throughputs in small tubular containers by introducing liquid cyanuric chloride through a nozzle in the upper portion of the mixing apparatus in countercurrent flow to upwardly flowing reactants plus acid binding agent introduced from at least one lower nozzle above a breast shaped constriction in the lower, open portion of the apparatus. The process can be carried out at normal, reduced or elevated pressure.

15 Claims, 3 Drawing Figures

4,259,487

PROCESS FOR THE PRODUCTION OF OPTIONALLY SUBSTITUTED 2-MERCAPTO-4,6-DI-CHLORO-S-TRIAZINES

BACKGROUND OF THE INVENTION 2-mercapto-4,6-dichloro-s-triazines and their substituent products are known intermediate products in the production of herbicides.

They are produced by starting with cyanuric chloride and reacting it with a mercaptan in the presence of an organic base or alkali compound such as soda lye, sodium carbonate or sodium bicarbonate or corresponding alkaline earth compounds as hydrogen chloride acceptors. (W. F. Beech, J. Chem. Soc., London, 1967 (c), page 470 et seq. The entire disclosure of the Beech article is hereby incorporated by reference and relied upon.)

According to another process as set forth in German Pat. No. 1670585 (the entire disclosure of which is hereby incorporated by reference and relied upon) the mercaptotriazines mentioned are obtained in very pure form and in high yields directly by carrying out the reaction in a heterogenous system which consists of water and at least one water immiscible organic solvent inert to cyanuric chloride. The temperature used was below the boiling point of the solvent.

Now it would be desirable to have a process in which the substituted 2-mercapto-4,6-dichloro-s-triazines are producible continuously in the reactor with high purity.

Through the very short residence time of the reactants in the reactor the by-products are reduced substantially and the yield and purity increased.

Figure 1:
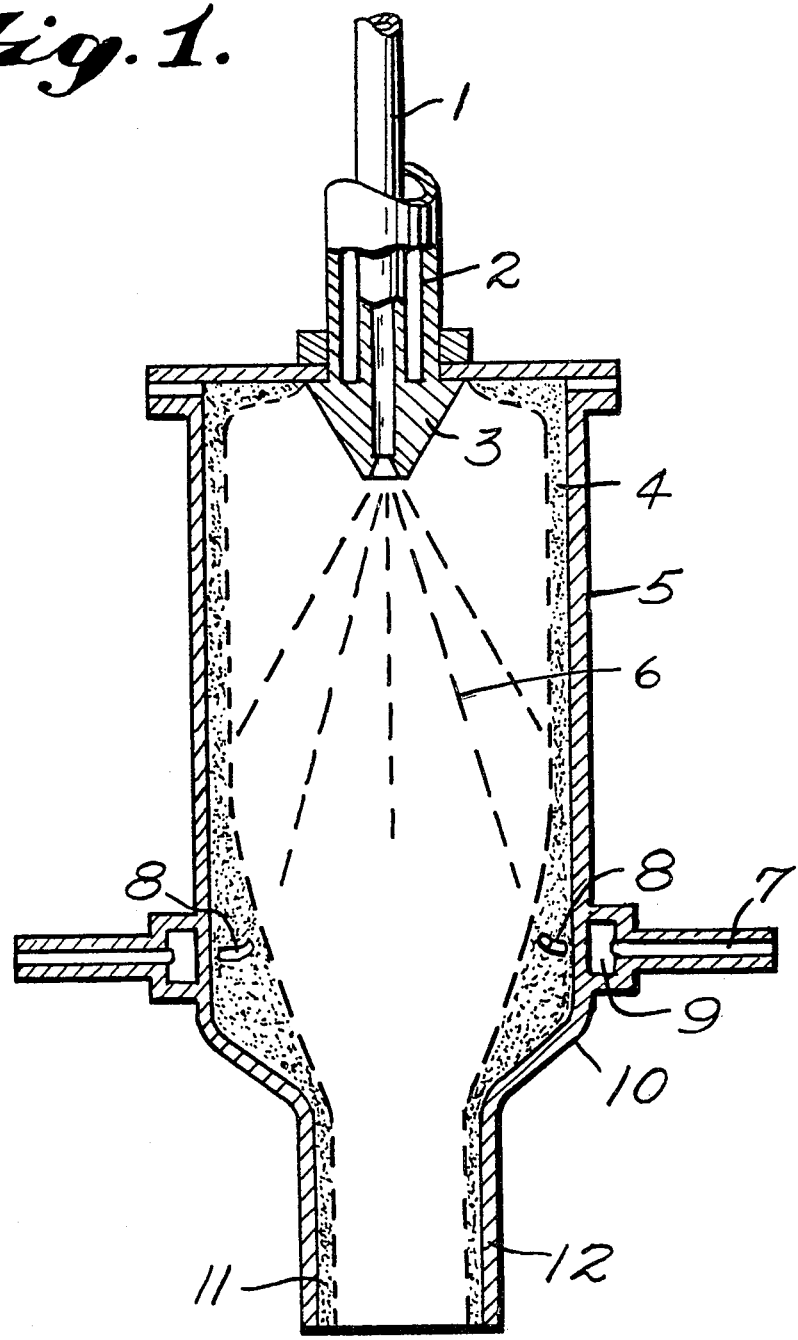
FIG. 1 is a vertical sectional elevation of one form of apparatus suitable for carrying out the process of the invention.

It has now been found that 2-mercapto-4,6-dichloro-s-triazines which in a given case are substituted can be produced continuously by reaction of cyanuric chloride with a mercaptan or mercaptide in the presence of an acid binding agent if liquid cyanuric chloride which is preferably free from chlorine and cyanogen chloride is sprayed into a container at temperatures in its molten range, if necessary in the presence of an inert gas, through a nozzle, preferably a spray nozzle, which is located in the head of a tubular container, during which this tubular container is closed or closeable at the top and downward constricted breast shaped to a discharge opening and with which the other reactant or reactants discharges through one or preferably several nozzles, preferably polished steel nozzles, which are located above the constriction and consist of one or more tangential spray agencies arranged in one or more rows which are arranged slightly above in the direction of the upper closing device or are arranged in the direction of the nozzle located in the upper portion and form a liquid layer along the entire chamber walls up to the nozzle for the cyanuric chloride, whereby the thickness of this layer at the breast shaped restriction is greater than at the rest of the chamber walls, and in which the sprayed cyanuric chloride enters.

The liquid cyanuric chloride is preferably introduced into the nozzle through a heated conduit.

By using the described apparatus it is possible to so distribute the mercaptan or mercaptide solvent and acid acceptor at the chamber walls that the liquid layer at the breast shaped constriction is thicker than at the remaining chamber walls.

By the expression used in the glass art: "breast shaped constriction" is meant a constriction which does not proceed steply, but in a flat S curve going from the wall of the tubular container to the disharge opening. Corresponding constrictions are also present in red win bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the mercaptan or mercaptide solvent and acid acceptor to be sure can be arranged at any place in the tubular container above the constriction, but preferably are located in the region directly above the breast shaped constriction.

As the tangentially arranged spray agencies, there can be used small tubes or nozzles as well as openings in the chamber walls or, with the presence of a feed ring, in its chamber walls.

Preferably there are used small tubes.

The tubular container described has the great advantage that it can be operated not only at an atmospheric pressure but also at reduced pressure. Thus without doing anything further it permits the adjustment proceeding from atmospheric pressure to reduced pressure of 0.01 bar.

At reduced pressure a portion of the solvent evaporates through which a cooling of the solution or suspension forming takes place. The mixing and reaction temperature in this way lets itself readily to a low level which is very essential for a continuous procedure.

As mercaptans which can be reacted with cyanuric chloride according to the process of the invention there can be employed all these known in the art, as e.g. the mercaptans of the general formula H—S—R or mercaptides of the fomula M—S—R mentioned in German Pat. No. 1670585 where R is a cycloalkyl, alkenyl, aralkyl or alkyl group with 1–18, preferably 1, carbon atoms which can be substituted by one or more alkoxy or alkyl mercapto groups with 1 to 4 carbon atoms and in which M is an alkali metal, e.g. sodium or potassium, or silver atom or is one valence of a mercury, zinc or lead atom.

Examples of mercaptans and mercaptides are methyl mercaptan, ethyl mercaptan, n-octyl mercaptan, allyl mercaptan, benzyl mercaptan, cyclohexyl mercaptan, octadecyl mercptan, n-butyl mercaptan, isobutyl mercaptan, sec-butyl mercaptan, methallyl mercaptan, methylthiomethyl mercaptan, butylthioethyl mercaptan, methoxyethyl mercaptan, methoxymethyl mercaptan, butoxymethyl mercaptan, crotyl mercaptan, lauryl mercaptan, cyclopentyl mercaptan and the corresponding mercaptides such as sodium methyl mercaptide, sodium ethyl mecaptide, sodium octyl mercaptide, sodium hexadecyl mercaptide, sodium octadecyl mercaptide, sodium benzyl mercaptides, sodium allyl mercaptide, potassium methyl mercaptide, potassium hexadecyl mercaptide, potassium octadecyl mercaptide, potassium benzyl mercaptide, silver methyl mercaptide, mercury di (methyl mercaptide), zinc di(methyl mercaptide), lead di(methyl mercaptide).

As acid binding agents there can likewise be used those known in the art such as those mention in German Pat. Nos. 1670585 and 1964619. Illustrative examples are alkali hydroxides such as sodium hydroxide or potassium hydroxide or alkali carbonates and bicarbonates such as sodium carbonate, potassium carbonate, sodium bicarbonate and potassium carbonate. There can also be employed organic bases such as collidine and pyridine as acid acceptors.

Since the cyanuric chloride is present in liquid form it is not necessary to employ a solvent for it, however, it is favorable that the mercaptan and above all the mercaptide be supplied to the nozzles in dissolved form. As solvents there are employed above all those set forth in German Pat. 1670585. There can also be employed mixtures of solvents. The temperatures and pH can be those mentioned in German Pat. No. 1670585.

As stated the solvent includes at least one water immiscible organic liquid which is inert to cyanuric chloride. Examples of such solvents include aromatic hydrocarbons, e.g. benzene, toluene, xylene or a mixture of $C_6$ to $C_9$ alkylated benzenes, chlorinated aromatic hydrocarbons, e.g. chlorobenzene, di or trichlorobenzene, nitrobenzene, phenol ethers, e.g. anisole, aliphatic hydrocarbons, e.g. pentane, hexane, decane, dialkyl ethers, e.g. dibutyl ether, dihexyl ether or diethyl ether, chlorinated aliphatic hydrocarbons, e.g. methylene chloride, chloroform or carbon tetrachloride, cycloaliphatic hydrocarbons, e.g. cyclohexane or decalin, nitriles, e.g. an aromatic nitrile such as toluonitrile, water immiscible esters, e.g. dimethyl succinate, aromatic ketones, e.g. acetophenone, tetralin.

A suitable apparatus for the recovery of the mentioned 2-mercapto-4,6-dichloro-s-triazines is described and claimed in German application No. 2850271.8-23 (and related U.S. Hentschel application Ser. No. 94,803, filed Nov. 15, 1979 and entitled "Apparatus For Brining Liquids In Contact", which is operated in the following manner.

As shown in FIG. 1 the liquid cyanuric chloride in supply line 1 is led through a coaxial heater 2 via a unary or binary nozzle 3 into the mixing chamber 5, i.e., the tubular container 5.

Figure 2:
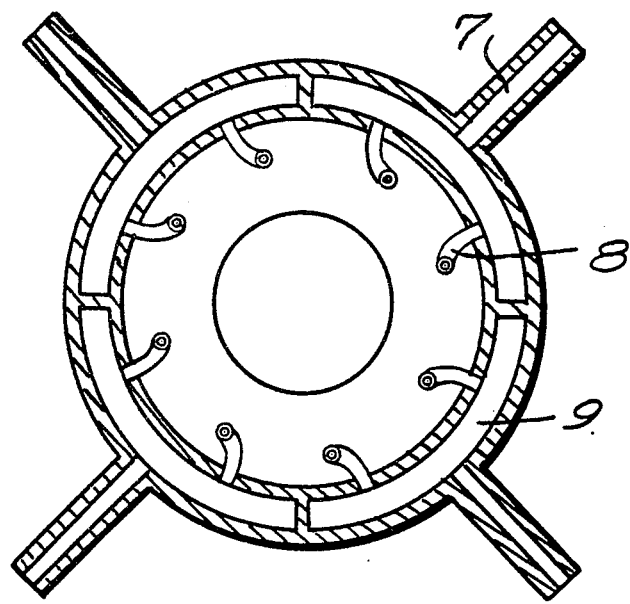
FIG. 2 is a cross-sectional view along the view 2—2 of FIG. 1.

The components being brought into contact with the sprayed material goes through separate supply lines 7 into a distribution ring having separate chamber segments 9, see also FIG. 2. The solvent is injected tangentially from these chamber segments via the slightly upwardly directed spray systems into the mixing chamber 5.

When using only one supply and only one spray organ, e.g. opening into the mixing chamber 5, the supply 7 passes directly into the spray opening 8 and the segmented chamber 9 is eliminated.

Besides the component in the circumferential direction the solvent jet has a velocity component in the axial direction. Therethrough the liquid reaches the wall of the mixing chamber 5. There it builds a liquid layer 4.

If the components are supplied through the supply lines 7, 8 and 9 into the mixing chamber 5, there occurs here an intensive thorough mixing of the supplied liquids, whose intensity can be increased still more by introducing a gas or vapors of the solent via the spray system 8.

The cyanuric chloride leaving the nozzle 3 is sprayed into the liquid layer 4. The spray angle for the cyanuric chloride sprayed out of nozzle 3 can be between 15° and 150°, preferably between 15° and 120°.

The shape of the spray varies from hollow or solid cone up to an unarranged mist, according to the type of nozzle.

Upon entering the spray particles 6 solidify and/or the sprayed cyanuric chloride dissolves in the liquid layer. The energy brought in is given up to the liquid layer, independent of the pressure in the tubular container.

The discharging mixture which leaves the tubular container 5 through the discharge opening 12 goes to the container 14 which can be connected if desired detachably, either directly or indirectly via line 13 to the discharge opening 12 of the container 5.

Figure 3:
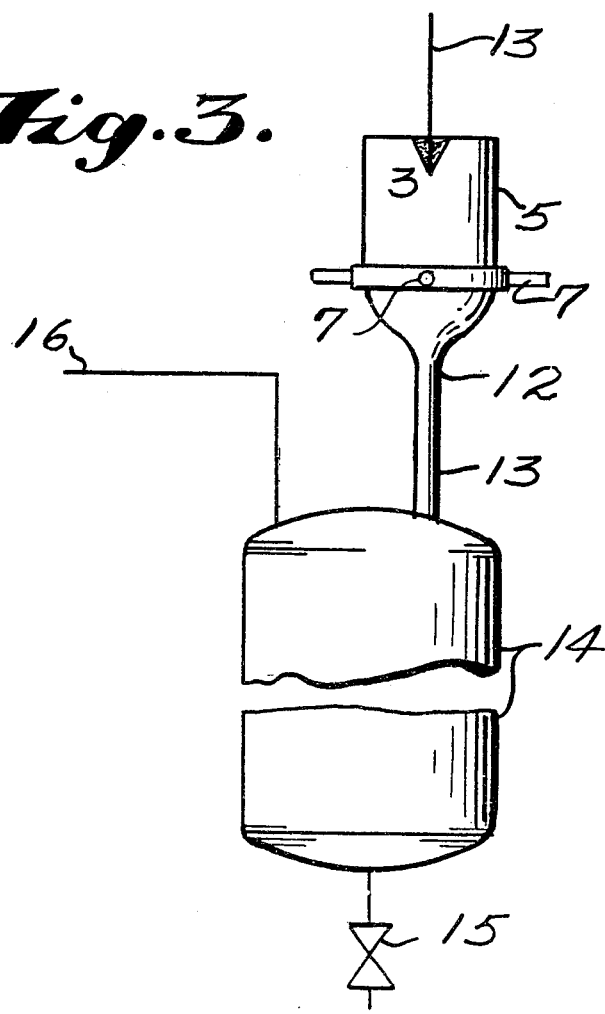
FIG. 3 is a schematic view of apparatus for carrying out the invention.

In this way it is possible to establish any desired pressure, i.e., any reduced or excess pressure, in the tubular container 5 and container 14 through known apparatus which is connected with the container 14 via line 16, see FIG. 3. (However, the known apparatuses for regulating the pressure are not shown in FIG. 3.)

The mixture is withdrawn at the discharge valve 15. The container 14, however, can in a given case also serve as reaction container for a further treatment or reaction.

However, it is also possible to apply reduced or superatmospheric pressure directly into the discharge line 13 through the known apparatuses and to transport away in known manner the discharging mixture from line 13 while eliminating an intermediate connection from container 14.

The apparatuses 5 and 14 shown in FIGS. 1 and 3, in a given case also line 13, can be heated or cooled in known manner, according to the requirements, see e.g. Ullmann, Enzyklopädie der technischen Chemie, Vol. 1, 3rd edition, 1951 pages 743–744 and 769–770.

Likewise there can be used for this purpose the known construction materials loc. cit.

The volume of the tubular container 5 is determined by the properties of the liquid used whereby the path of the sprayed particles 6 up to the impingement on the liquid layer 4 should be held as short as possible.

Through this it is possible to carry out relatively large througputs in a very small tubular container, e.g. the volume in Example 1 is about 0.5 liters. By establishing a specific pressure, e.g., a reduced pressure in mixing chamber 5, the heat energy of the sprayed cyanuric chloride and the heat of reaction in contact with the liquid layer can be removed.

The product produced leaves the mixing chamber through the discharge outlet 12.

To improve the formation of the liquid layer the spray systems 8 tangential to the mixing chamber are directly slightly upwardly. The exact angle of bending is so adjusted according to the components that the liquid layer reaches up to the nozzle, but does not touch it.

Through the breast shaped constriction and the thicker liquid layer produced at this wall position thereby there results, despite the outlet opening, that the remaining chamber walls always are covered with a uniform, i.e. uninterrupted layer of liquid. Through this there is guaranteed a high mixing velocity.

The spray cone of the liquid cyanuric chloride is designated by the number 6.

The number of inlet lines 7 depends on the particular case.

Thus in feeding in only a single material one supply line is sufficient, however, for better distribution of this material there has also proven as desirable to use several supply lines, see for example FIG. 2; even using several components which also can be simultaneously introduced as a mixture the distribution ring described for example in FIG. 2 is suitable.

Liquid cyanuric chloride can be obtained according to known process, e.g. according to Geiger, German Pat. No. 2,322,636 and related Geiger U.S. Pat. No. 3,925,377. The entire disclosure of the Geiger U.S. patent is hereby incorporated by reference and relied upon.

Preferably according to the process of the invention there is employed a liquid cyanuric chloride whose temperature is 170° C. and which is free from chlorine and cyanogen chloride. For freeing from chlorine and cyanogen chloride known processes are suitable, as e.g. dephlegmatization.

According to the process of the invention it is possible to produce mercapto-s-triazines, which in a given case are mono substituted, continuously and with higher yields than is otherwise possible.

Unless otherwise indicated all parts and percentages are by weight.

The process can comprise, consist essentially of or consist of the steps set forth and the materials can comprise, consist essentially of or consist of those set forth. The apparatus can comprise, consist essentially of or consist of the parts set forth.

The invention will be further explained through the following examples.

DESCRIPTION OF THE PREFERRED EMBODIMENTS

Example 1

Liquid cyanuric chloride at about 170° C. is led via the heated supply line 1 into the unary nozzle 3. The nozzle 3 has a bore of 0.8 mm and a spray angle of about 70°. The supply pressure of the melt was 4 bar. There were sprayed 45 kg/h of liquid cyanuric chloride into the mixing chamber 5. This mixing chamber 5 has a diameter of 80 mm and atmospheric pressure prevailed in it.

Methylene chloride in an amount of 585 liters/h entered the mixing chamber 5 through two supply lines 7 lying opposite to each other and through the other two supply lines 7 there were introduced into the mixing chamber 60 liters/h of an aqueous sodium methyl mercaptide solution which contained 16.8 kg of sodium methyl mercaptide. The reaction mixture which was discharged had a temperature of about 20° C. The 2-methylmercapto-4,6-dichloro-s-triazine can be isolated from the organic phase in a yield of about 96%. The content of 2,4-dimethylmercapto-6-chloro-s-triazine was about 5%

Example 2

In a comparison experiment there were present in a 2 liter multinecked flask 184.4 grams of cyanuric chloride dissolved in 760 grams of toluene and there were dropped in at about 40°-50° C. in the course of 1 hour 252 ml of an aqueous sodium methyl mercaptide solution which contained 70.1 grams of sodium methyl mercaptide. From the organic phase there could be isolated about 90% of 2-methylmercapto-4,6-dichloro-s-triazine. The content of 2,4-dimethylmercapto-6-chloro-s-triazine was about 10%.

Example 3

The procedure of Example 1 was followed with the change that instead of methylene chloride there was employed toluene. The discharging reaction mixture had a temperature of about 23° C. The results of the experiment were the same as in Example 1.

The entire disclosure of German priority application No. P2850332.4-44 is hereby incorporated by reference.

What is claimed is:

1. A process for the production of a 2-mercapto-4,6-dichloro-s-triazine or a substituted 2-mercapto-4,6-dichloro-s-triazine by reacting a mercaptan or mercaptide with cyanuric chloride in the presence of an acid binding agent comprising spraying cyanuric chloride at a temperature in its molten range through a nozzle located in the upper portion of a tubular container into the container said container being closed or closeable at the top and being breast-shaped constricted downwardly to form a discharge opening, discharging the other reactants or components through at least one nozzle located above the constriction and out of at least one spray system arranged tangentially in at least one series and which is directed slightly upwardly in the direction of the upper closing device or nozzles located in the upper portion and forming thereby a liquid layer along the entire container wall up to the nozzle for supplying cyanuric chloride, whereby the thickness of this layer at the breast-shaped constriction is greater than in the remainder of the container walls, and in which liquid layer the sprayed cyanuric chloride enters.

2. The process of claim 1 wherein the liquid cyanuric chloride employed is free from chlorine or cyanogen chloride.

3. The process of claim 2 wherein there are employed a plurality of nozzles to introduce the water containing organic solvent.

4. The process of claim 1 wherein there is employed a mercaptan of the formula H—S—R or a mercaptide of the formula M—S—R in which R is cycloalkyl, alkenyl, aralkyl or alkyl with 1-18 carbon atoms or such a mercaptide substituted with an alkoxy or alkylmercapto group containing 1-4 carbon atoms and where M is an alkali metal atom, silver atom or a valence of mercury, zinc or lead atom.

5. The process of claim 4 wherein the compound employed is a mercaptan of the formula H—S—R.

6. The process of claim 5 where R is alkyl.

7. The process of claim 6 where R is methyl.

8. The process of claim 4 wherein the compound employed is a mercaptide of the formula M—S—R.

9. The process of claim 8 where R is alkyl.

10. The process of claim 9 where M is an alkali metal atom.

11. The process of claim 10 where R is methyl.

12. The process of claim 11 where the alkali metal atom is the sodium atom.

13. The process of claim 1 including reducing the pressure to between below atmospheric pressure and 0.01 bar and thereby lowering the mixing temperature.

14. A process according to claim 1 comprising discharging the solution or suspension formed to another container adapted for use at subatmospheric or superatmospheric pressure.

15. A process for the production of a 2-mercapto-4,6-dichloro-s-triazine or a substituted 2-mercapto-4,6-dichloro-s-triazine by reacting a mercaptan or mercaptide with cyanuric chloride in the presence of an acid binding agent comprising spraying cyanuric chloride downwardly and outwardly at a temperature in its molten range from the upper portion of a vertical tubular zone closed at the top thereof to contact and mix with the mercaptan or mercaptide and components which form a liquid layer defining said tubular zone, constricting said layer in breast-shaped manner downwardly below the place of entry of the cyanuric chloride into the tubular zone to form a narrower discharge opening, discharging said mercaptan or mercaptide and other components as a spray tengentially to said layer and directed slightly upwardly in the direction of the closed top above said constriction and below the point of introduction of the cyanuric chloride and thereby forming said liquid layer along the entire tubular zone to the point of introduction of the cyanuric chloride, whereby the thickness of said layer where it is formed into a breast-shaped constriction is greater than it is in the remainder of the tubular zone.

* * * * *